（12）United States Patent
Woloszko et al.

(10) Patent No.: US 10,675,080 B2
(45) Date of Patent: Jun. 9, 2020

(54) SYSTEM AND METHODS OF CONTROLLING TEMPERATURE RELATED TO ELECTROSURGICAL PROCEDURES

(71) Applicant: Smith & Nephew, Inc., Austin, TX (US)

(72) Inventors: Jean Woloszko, Austin, TX (US); Jonathan L. Gaspredes, Austin, TX (US); Thomas P. Ryan, Austin, TX (US)

(73) Assignee: Smith & Nephew, Inc., Austin, TX (US)

( * ) Notice: Subject to any disclaimer, the term of this patent is extended or adjusted under 35 U.S.C. 154(b) by 508 days.

(21) Appl. No.: 15/342,413

(22) Filed: Nov. 3, 2016

(65) Prior Publication Data

US 2017/0143401 A1    May 25, 2017

Related U.S. Application Data

(60) Provisional application No. 62/259,827, filed on Nov. 25, 2015.

(51) Int. Cl.
*A61B 18/14* (2006.01)
*A61B 18/04* (2006.01)
(Continued)

(52) U.S. Cl.
CPC ........ *A61B 18/042* (2013.01); *A61B 18/1206* (2013.01); *A61B 18/1233* (2013.01);
(Continued)

(58) Field of Classification Search
CPC .............. A61B 18/042; A61B 18/1206; A61B 18/1233; A61B 18/14; A61B 18/148;
(Continued)

(56) References Cited

U.S. PATENT DOCUMENTS 6,635,034 B1 * 10/2003 Cosmescu .............. A61B 18/14
  601/35
7,311,708 B2 * 12/2007 McClurken ........ A61B 18/1492
  606/50

(Continued)

FOREIGN PATENT DOCUMENTS

WO    03/020339    3/2003
WO    2014/137342    9/2014

OTHER PUBLICATIONS

International Search Report and The Written Opinion for PCT/US2016/060292 dated Feb. 9, 2017, 14 pages.

*Primary Examiner* — Michael F Peffley
*Assistant Examiner* — Amanda L Zink
(74) *Attorney, Agent, or Firm* — Norman F. Hainer, Jr.

(57) ABSTRACT

Electrosurgical procedures. At least some of the example methods for detecting that an electrosurgical wand is effected by a blockage, including supplying a high frequency energy to an active electrode of an electrosurgical wand; drawing an electrically conductive fluid from the vicinity of the active electrode; sensing a temperature signal indicative of a temperature of the electrically conductive fluid drawn from the vicinity of the active electrode; and cycling the high frequency energy supplied upon the temperature of the electrically conductive fluid drawn from the vicinity of the active electrode exceeding a first threshold temperature.

21 Claims, 9 Drawing Sheets

(51) Int. Cl.
*A61B 18/12* (2006.01)
*A61B 18/00* (2006.01)

(52) U.S. Cl.
CPC ............ *A61B 18/14* (2013.01); *A61B 18/148* (2013.01); *A61B 2018/00011* (2013.01); *A61B 2018/00607* (2013.01); *A61B 2018/00642* (2013.01); *A61B 2018/00666* (2013.01); *A61B 2018/00702* (2013.01); *A61B 2018/00714* (2013.01); *A61B 2018/00732* (2013.01); *A61B 2018/00744* (2013.01); *A61B 2018/00767* (2013.01); *A61B 2018/00791* (2013.01); *A61B 2218/001* (2013.01); *A61B 2218/007* (2013.01)

(58) Field of Classification Search
CPC ........... A61B 2018/00011; A61B 2018/00607; A61B 2018/00642; A61B 2018/00666; A61B 2018/00702; A61B 2018/00714; A61B 2018/00732; A61B 2018/00744; A61B 2018/00767; A61B 2018/00791; A61B 2218/001; A61B 2218/007
See application file for complete search history.

(56) References Cited

U.S. PATENT DOCUMENTS

| | | | |
|---|---|---|---|
| 8,192,424 B2* | 6/2012 | Woloszko | A61B 18/1206 604/28 |
| 9,713,489 B2 | 7/2017 | Woloszko et al. | |
| 9,907,599 B2* | 3/2018 | Hoey | A61B 18/04 |
| 2008/0167646 A1* | 7/2008 | Godara | A61B 18/1477 606/41 |
| 2011/0270242 A1* | 11/2011 | Marion | A61B 18/148 606/35 |
| 2012/0215213 A1* | 8/2012 | Juzkiw | A61B 18/14 606/33 |
| 2014/0257269 A1 | 9/2014 | Woloszko et al. | |
| 2017/0065343 A1* | 3/2017 | Mickelsen | A61B 18/1492 |

* cited by examiner

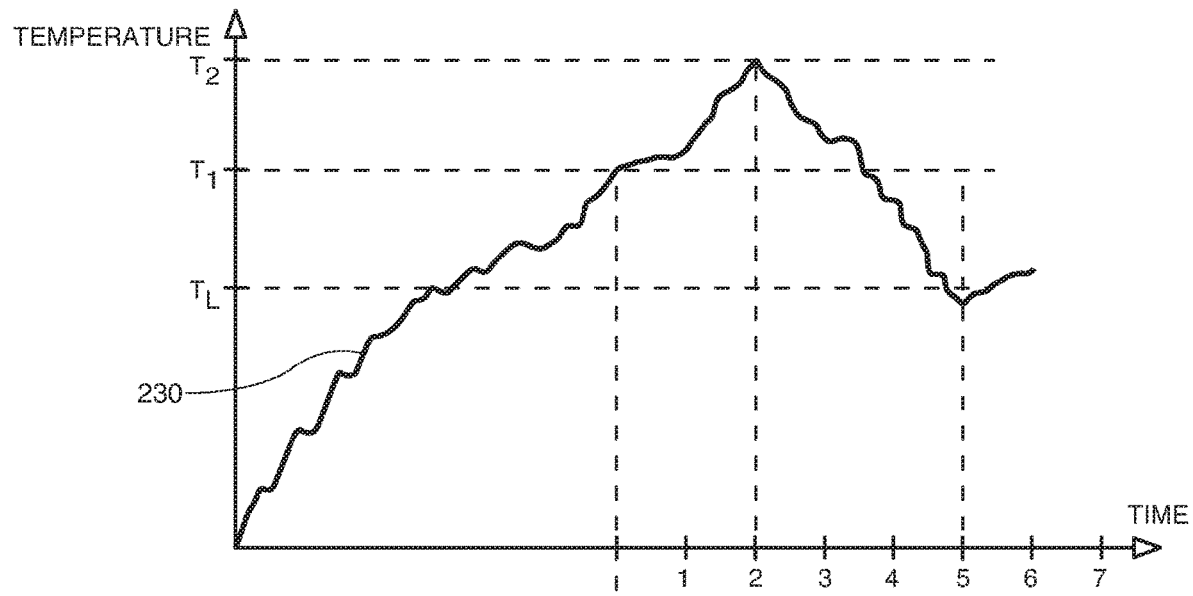
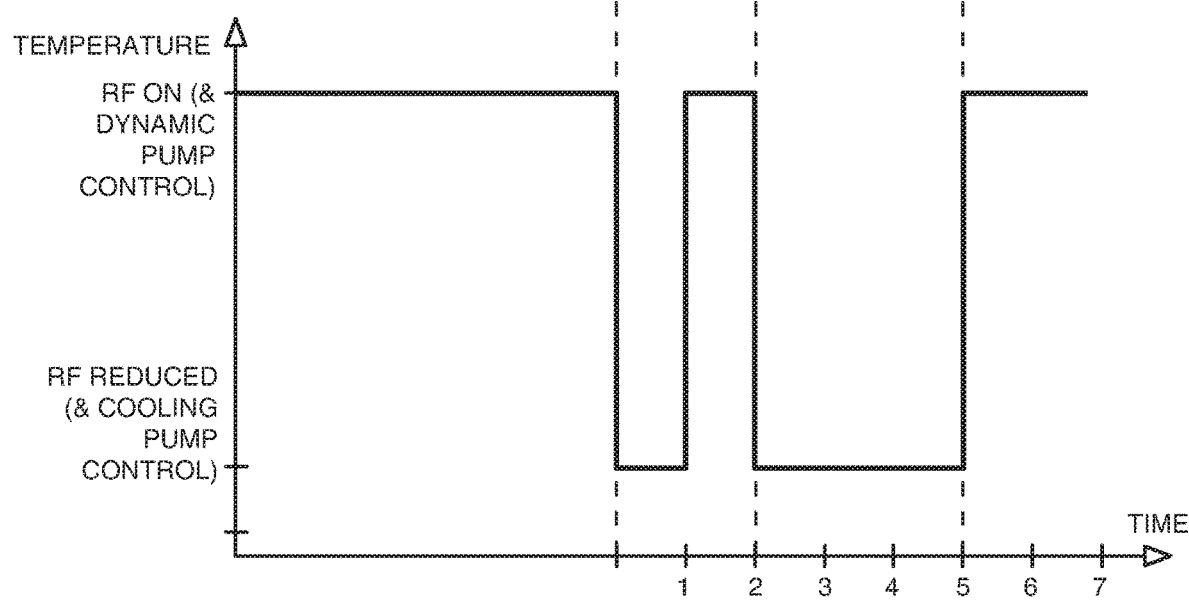

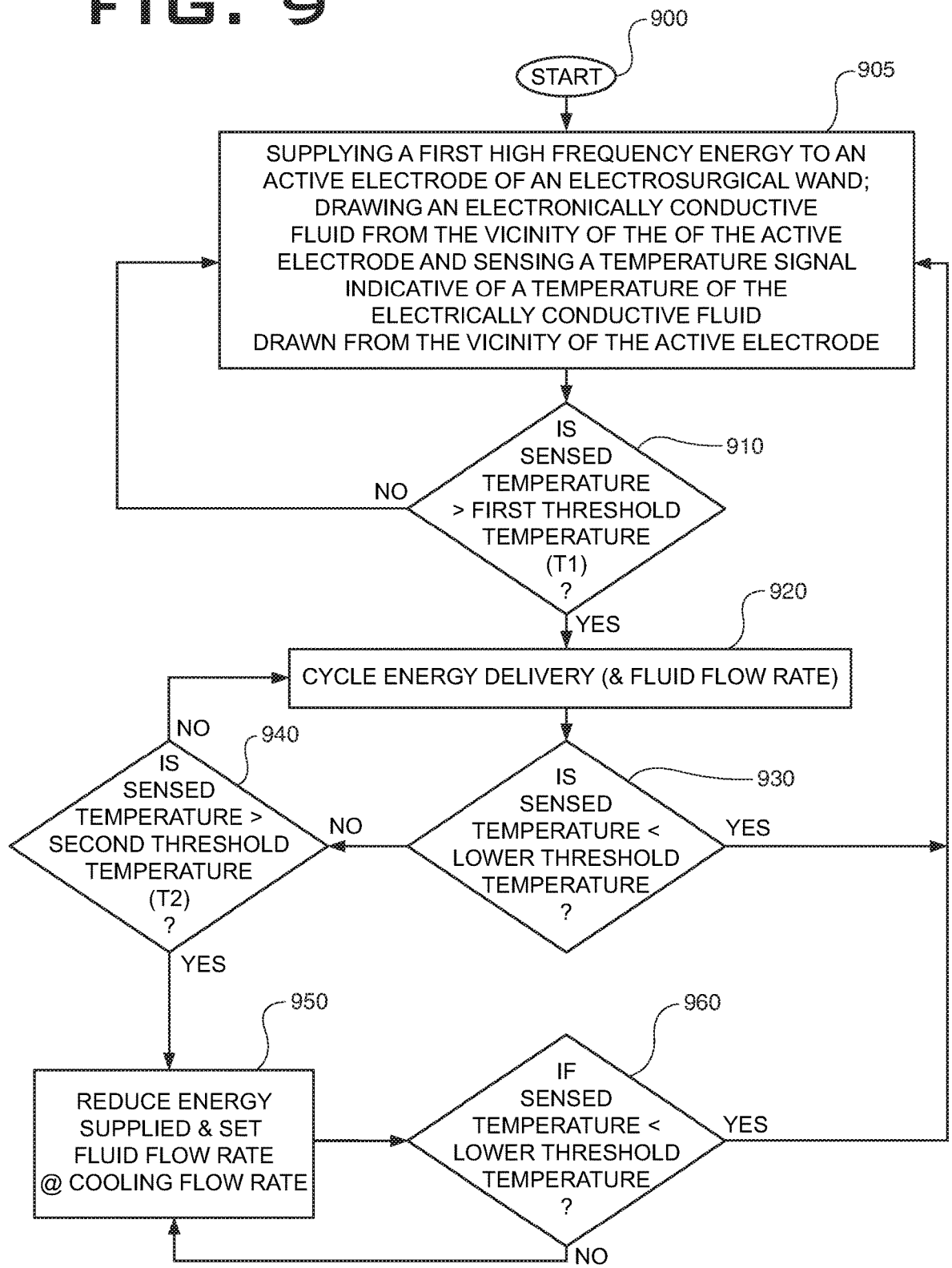

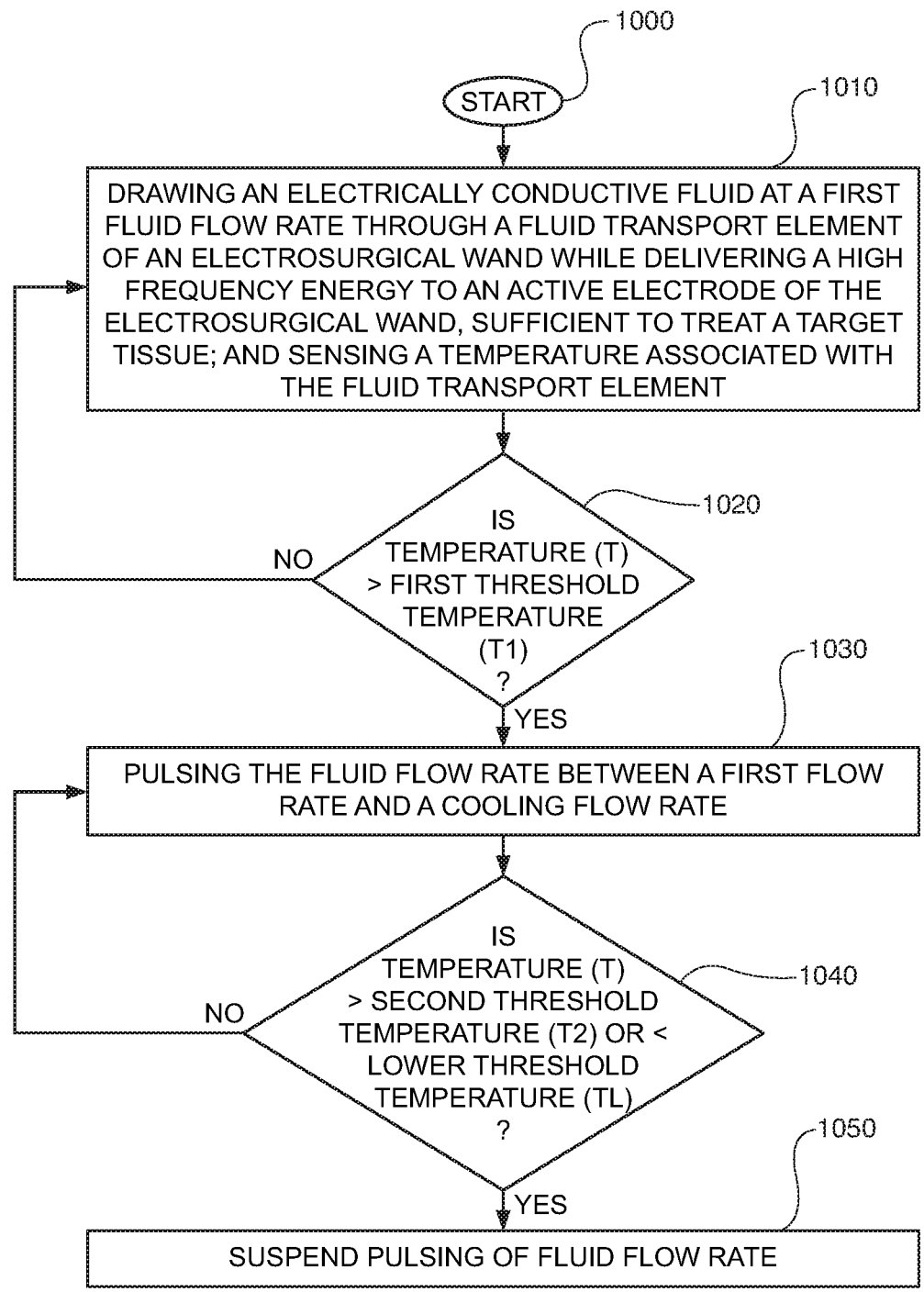

SYSTEM AND METHODS OF CONTROLLING TEMPERATURE RELATED TO ELECTROSURGICAL PROCEDURES

CROSS-REFERENCE TO RELATED APPLICATIONS

This application claims priority to U.S. provisional application No. 62/259,827, filed Nov. 25, 2015, entitled "Systems and Methods of Controlling Temperature", which the entirety is incorporated by reference herein.

FIELD OF THE INVENTION

The present invention relates to systems and methods for limiting temperatures of components associated with energy based instruments that treat tissue at surgical sites; components such as fluid aspiration tubes and the fluid associated with said tubes. More particularly, the present invention relates to methods and apparatus for measuring and limiting temperatures of a fluid transport tube associated with an electrosurgical wand.

BACKGROUND OF THE INVENTION

The field of electrosurgery includes a number of loosely related surgical techniques which have in common the application of electrical energy to modify the structure or integrity of patient tissue. Electrosurgical procedures usually operate through the application of very high frequency currents to cut or ablate tissue structures, where the operation can be monopolar or bipolar. Monopolar techniques rely on a separate electrode for the return of RF current that is placed away from the surgical site on the body of the patient, and where the surgical device defines only a single electrode pole that provides the surgical effect. Bipolar devices comprise both electrodes for the application of current between their surfaces.

Electrosurgical procedures and techniques are particularly advantageous since they generally reduce patient bleeding and trauma associated with cutting operations. Additionally, electrosurgical ablation procedures, where tissue surfaces and volume may be reshaped, cannot be duplicated through other treatment modalities.

Generally, radiofrequency (RF) energy is used during arthroscopic procedures because it provides efficient tissue resection and coagulation and relatively easy access to the target tissues through a portal or cannula. However, a typical phenomenon associated with the use of RF during these procedures is that the currents used to induce the surgical effect can result in heating of fluid in the area. While some minimal heating of the fluid may occur as the fluid flows over an active electrode of an energy based device, this fluid is typically effectively removed via evacuation of the fluid through tubing or aspiration elements associated with the device or disposed adjacent the device. However if the flow of fluid is disrupted or reduced, possibly due to a clog, the fluid may be exposed to the electrical current delivered to the electrode for longer periods of time, thereby increasing fluid temperatures. This heated fluid could potentially transfer high temperatures through the fluid transport walls of the tube or transport element to other portions of the device adjacent the tube, such as mechanical and electrical components, potentially damaging the device. In addition heated fluid may transfer high temperatures through suction tubing walls extending from the device, the suction tubing potentially laying across and coming into contact with the patient or surgeon along its path and potentially causing patient or surgeon burns.

Fluid flow may be inadequate or disrupted, elevating fluid temperatures for a variety of reasons. For example, the surgeon may be pushing the device up against tissue, preventing adequate fluid flow volume through an aspiration aperture. Alternatively the flow system may have been set at an insufficient setting or pressure for the energy setting of the energy delivery system. This reduced volume of fluid may more readily warm and therefore increase the overall temperature of the fluid aspirated. As a further example, debris may sometimes partially clog the aspiration aperture or aspiration lumen, again reducing the flow. This hotter fluid may then increase the temperature of the device and particularly the outer wall of the aspiration tubing walls, potentially causing instrument failure or injury to the patient or attending medical staff. Of note however, should the fluid flow system become completed clogged, eliminating most of the flow, the temperature may drop. This over-temperature system and method disclosed here does not expressly detect a complete clog of the system. An improved system and method to sense, limit and actively reduce the temperature of the fluid being drawn through the device and thereby the temperature of the tubing is desired.

SUMMARY OF THE INVENTION

During the treatment of a target tissue using energy, a system is disclosed including a probe and a controller. The probe has at least one temperature sensor positioned in, or adjacent fluid in the region spaced proximal of an electrode assembly and spaced away from the target tissue; the controller is operable to receive a temperature signal from the at least one temperature sensor indicative of the temperature of the fluid. The temperature sensor may be disposed within the probe handle, abutting an outer wall of suction tubing for example. Alternatively, the temperature sensor may be located within the suction lumen of the probe, or within the tubing. The controller may also control a fluid pump, adjusting the flow of fluid through the probe and through the suction lumen associated with the probe. The controller is further operable to automatically pulse, suspend or reduce delivery of the energy to the active electrode terminal of the probe should a threshold signal be received indicative of reaching a threshold temperature. The controller may simultaneously adjust the fluid flow rate through the device should a threshold signal be received indicative of reaching this threshold temperature. The temperature of the electrically conductive fluid is calculated or estimated by the controller based on the monitored temperature signal.

Another embodiment discloses a method for ablating tissue at a target site comprises positioning a distal end of an electrosurgical instrument adjacent to the tissue to be treated. High frequency energy is applied to the tissue via the instrument and fluid is flowed through the instrument and through tubing extending from a handle of the instrument. The method further includes sensing a temperature of the electrically conductive fluid being drawn from the instrument distal end, the temperature sensor spaced proximally from the instrument distal end and automatically adjusting either or both the high frequency energy delivered and the flow of fluid through the instrument should the sensed temperature indicate a temperature above a first threshold temperature. This temperature may be one that approaches a level that may cause injury or damage on contact with a device or person. In one embodiment the high frequency energy and the flow rate of the fluid may be automatically pulsed if the sensed temperature reaches this first threshold temperature. Adjusting the fluid flow rate may be performed by, for example pulsing the fluid flow through an aspiration aperture of the device sufficient to aid in cooling the device and tubing, but not sufficient to draw significant debris and tissue disposed at the target site through device.

In one embodiment disclosed, upon a signal indicative of a first threshold temperature (T1) being received, a first over-temperature cycle may be initiated, until a signal indicative of a lower threshold temperature ($T_L$) is received. The first over-temperature cycle may include alternating periods of energy delivery suspension with periods of energy delivery. Energy delivery suspension may include significantly reducing the energy to a level that aims to limit any further temperatures increase, the period of energy delivery suspension having a duration that may be automatically adjustable and may last between 0.5-5 seconds, and preferably approximately for 1 second. An alarm, audible or visual may be indicated to the user that a first over-temperature cycle has been initiated. The first over-temperature cycle may also include alternating periods of cycling the fluid flow rate between a first flow rate and a cooling flow rate, so as to aid in cooling the components adjacent the temperature sensor. The cooling flow rate may be higher or lower than the first flow rate. During the first over-temperature cycle, after the period of suspended energy delivery, high frequency energy may be delivered and fluid may be caused to flow through the device sufficient to treat tissue and may cooperate so as to form a plasma according to the desired setting or mode of the device, for a period of between 0.5-5 seconds, and preferably around 1 second, before the energy may be suspended or reduced once again. This cycling may be repeated until the temperature signal indicates that the temperature has dropped below a lower threshold value ($T_L$), at which point high frequency energy may be delivered and fluid may flow, sufficient to treat tissue without interruption or suspension.

However, if after initiating the first over-temperature cycle as described above, the temperature continues to increase, and if a signal indicative of a second (higher) upper threshold temperature (T2) has been received, a second over-temperature cycle may be initiated until the signal indicative of the lower threshold temperature ($T_L$) is received. The second cycle may suspend or adjust energy delivery to a level that does not treat tissue or significantly heat fluid for a period extending up until the signal indicative of a lower threshold temperature ($T_L$) is received. No energy or reduced energy may be delivered at this time, and unlike the first cycle described above, energy delivery may not cycle or pulse. During this time, fluid may also be controlled so as to flow at a rate sufficient to aid in cooling the components adjacent the temperature sensor.

In another embodiment, treating tissue includes forming a plasma in the vicinity of the active electrode of the electrosurgical probe thereby causing ablation of the soft tissue.

In another embodiment, the method is performed wherein the target site is a joint.

In a further embodiment, a method of limiting a temperature of a fluid transport element associated with an electrosurgical wand is disclosed, wherein a first high frequency energy is supplied to an active electrode of an electrosurgical wand, while drawing an electrically conductive fluid within a first flow rate range from the vicinity of the active electrode. The first flow rate range may be dynamically controlled so as to maintain an electrode circuit impedance of the wand within a predetermined range. A temperature signal indicative of a temperature of the electrically conductive fluid drawn from the vicinity of the active electrode may also be sensed, the temperature sensor in operational relationship with a suction tubing associated with the wand. Should the temperature sensor indicate that the fluid temperature is increasing, this may be an indication of a partial blockage of the suction tubing, and should this temperature reach or exceed a first threshold value, the high frequency energy and the aspiration rate at which the electrically conductive fluid is drawn may be pulsed so as to limit the heating of the fluid. Pulsing the flow rate may include pulsing between the first flow rate range and a cooling flow rate; the cooling flow rate configured to draw fluid at a rate sufficient to aid in reducing the sensed temperature with limited debris aspiration. Pulsing may still continue to provide a tissue effect at the active electrode sufficient to treat tissue, and may continue to form a plasma at times.

Should the pulsing not limit the temperature sensed and should the temperature continue to elevate to a second threshold temperature (T2), the high frequency energy supplied and fluid flow rate may cease pulsing and adjust to a reduced energy level and constant cooling flow rate. This reduced energy level may no longer treat tissue. The cooling flow rate may be a high flow rate capable of removing a partial blockage in the aspiration tubing of the device, or may alternatively just be sufficient to cool the tubing and adjacent components while providing minimal debris aspiration. Once the second threshold limit has been sensed, the system may be limited to supply energy that does not affect tissue until a lower threshold limit has been sensed ($T_L$), that is lower than either the first or second threshold temperatures (T1 or T2)

In a further embodiment, a method of limiting a temperature of an electrically conductive fluid drawn through a fluid transport element of an electrosurgical wand is disclosed wherein the electrically conductive fluid is drawn at a first fluid flow rate though the fluid transport element while a high frequency energy is delivered to an active electrode of the electrosurgical wand, sufficient to treat a target tissue and a temperature associated with the fluid transport element is sensed. Should a temperature above a first threshold temperature be indicated, the electrically conductive fluid flow may be cycled between the first fluid flow rate and a cooling flow rate, and should a second, higher threshold temperature be sensed or a lower threshold temperature be sensed, pulsing the electrically conductive fluid flow rate may be suspended.

A further embodiment may include a system having a controller with a processor, a memory coupled to the processor, a voltage generator operatively coupled to the processor and a fluid flow pump operatively coupled to the processor. The system also includes an electrosurgical wand operatively coupled to an output of the voltage generator, the wand having a temperature sensor in operational relationship with a fluid transport element associated with the electrosurgical wand; the temperature sensor communicatively coupled to the processor. The memory may store a program that, when executed by the processor, causes the controller to deliver a first high frequency voltage to an active electrode of the electrosurgical wand while controlling the pump to draw an electrically conductive fluid through the fluid transport element at a first flow rate range from the vicinity of the active electrode and sensing a temperature signal indicative of a temperature of the electrically conductive fluid drawn from the vicinity of the active electrode. The memory may store a program that, when executed by the processor, is configured to cause the controller to control the fluid pump and voltage generator so as to pulse the voltage supplied and the electrically conductive fluid drawn upon the processor receiving a signal indicative that the temperature of the electrically conductive fluid drawn from the vicinity of the active electrode exceeds a first threshold temperature.

The description, objects and advantages of the present invention will become apparent from the detailed description to follow, together with the accompanying drawings.

BRIEF DESCRIPTION OF THE DRAWINGS

For a detailed description of exemplary embodiments, reference will now be made to the accompanying drawings in which:

FIG. 8A is an illustrative graph showing a signal indicative of temperature versus time;

FIG. 8B is an illustrative graph showing changes in the RF and pump control system upon the temperature signal reaching a first and second threshold temperature (T1 and T2); and FIG. 9 shows a flow diagram in accordance with at least some embodiments.

FIG. 10 shows a flow diagram in accordance with at least some embodiments.

NOTATION AND NOMENCLATURE

Figure 1:
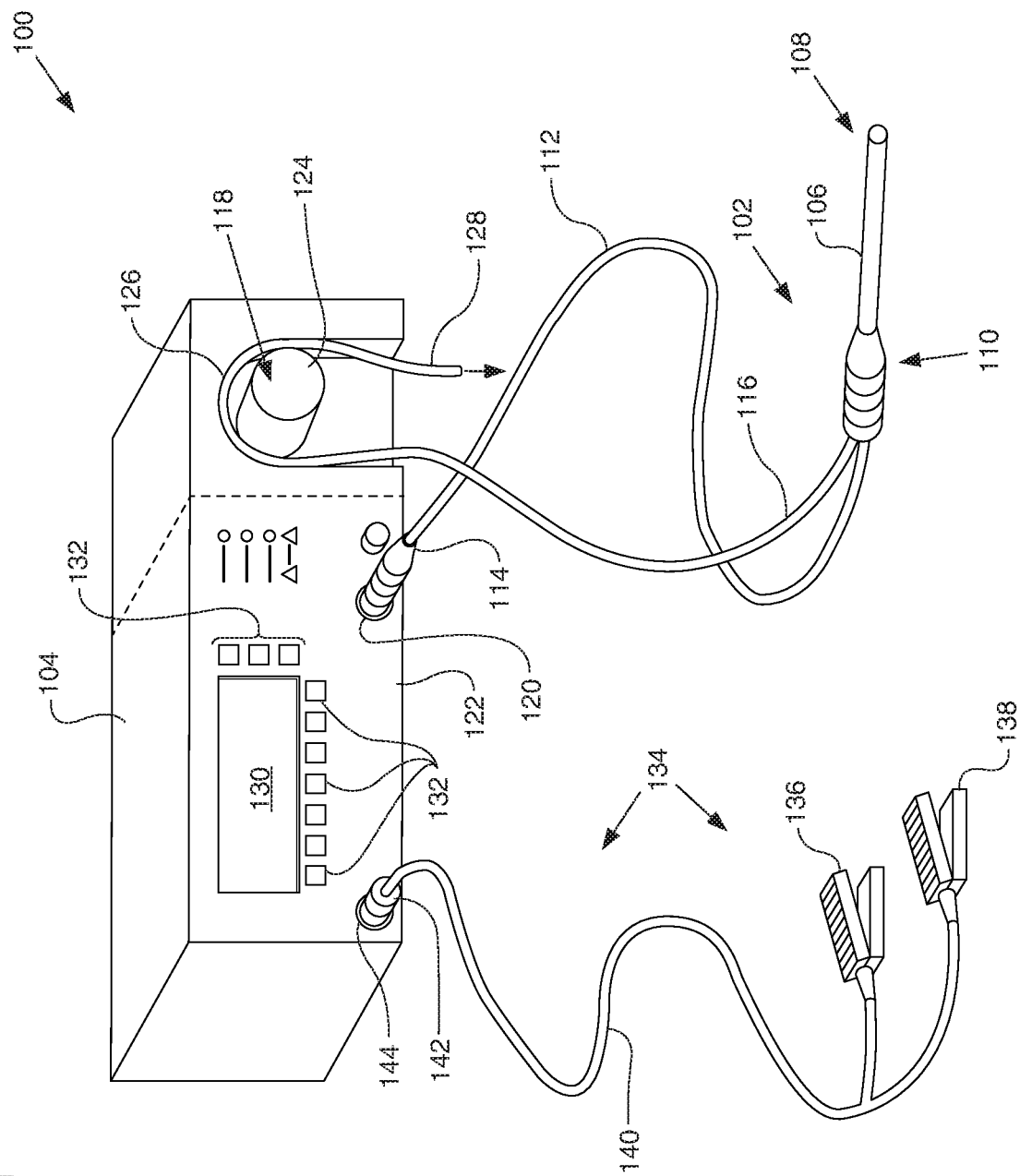
FIG. 1 shows an electrosurgical system in accordance with at least some embodiments.

Certain terms are used throughout the following description and claims to refer to particular system components. As one skilled in the art will appreciate, companies that design and manufacture electrosurgical systems may refer to a component by different names. This document does not intend to distinguish between components that differ in name but not function.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

Reference to a singular item includes the possibility that there are plural of the same items present. More specifically, as used herein and in the appended claims, the singular forms "a," "an," "said" and "the" include plural references unless the context clearly dictates otherwise. It is further noted that the claims may be drafted to exclude any optional element. As such, this statement serves as antecedent basis for use of such exclusive terminology as "solely," "only" and the like in connection with the recitation of claim elements, or use of a "negative" limitation. Lastly, it is to be appreciated that unless defined otherwise, all technical and scientific terms used herein have the same meaning as commonly understood by one of ordinary skill in the art to which this invention belongs.

"Ablation" shall mean removal of tissue based on tissue interaction with a plasma.

"Mode of ablation" shall refer to one or more characteristics of an ablation. Lack of ablation (i.e., a lack of plasma) shall not be considered a "mode of ablation." A mode which performs coagulation shall not be considered a "mode of ablation."

"Active electrode" shall mean an electrode of an electrosurgical wand which produces an electrically-induced tissue-altering effect when brought into contact with, or close proximity to, a tissue targeted for treatment.

"Return electrode" shall mean an electrode of an electrosurgical wand which serves to provide a current flow path for electrical charges with respect to an active electrode, and/or an electrode of an electrical surgical wand which does not itself produce an electrically-induced tissue-altering effect on tissue targeted for treatment.

"Electric motor" shall include alternating current (AC) motors, direct current (DC) motors, as well as stepper motors.

"Controlling flow of fluid" shall mean controlling a volume flow rate. Control of applied pressure to maintain a set point pressure (e.g., suction pressure) independent of volume flow rate of liquid caused by the applied pressure shall not be considered "controlling flow of fluid." However, varying applied pressure to maintain a set point volume flow rate of liquid shall be considered "controlling flow of fluid".

"Impedance" shall mean complex impedance (or any portion thereof, e.g., the real portion, the imaginary portion) of an electrode circuit, including the plasma created and maintained in operational relationship to an active electrode of a wand, fluid between the active and return electrode, and the electrode-fluid interface.

A proximity that is in "operational relationship with tissue" shall mean a proximity wherein the tissue interacting with a plasma affects the impedance presented by the plasma to electrical current flow through the plasma.

A fluid conduit said to be "within" an elongate shaft shall include not only a separate fluid conduit that physically resides within an internal volume of the elongate shaft, but also situations where the internal volume of the elongate shaft is itself the fluid conduit.

A "temperature measurement device" shall mean a device capable of sensing a temperature, and may include a sensor or number of sensors, thermocouples, thermistors, fiber optic (i.e. optical), or resistance temperature detectors (RTD). The device output may be a signal indicative of the temperature.

Where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

DETAILED DESCRIPTION

Before the various embodiments are described in detail, it is to be understood that this invention is not limited to particular variations set forth herein as various changes or modifications may be made, and equivalents may be substituted, without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

FIG. 1 illustrates an electrosurgical system 100 in accordance with at least some embodiments. In particular, the electrosurgical system 100 comprises an electrosurgical wand 102 (hereinafter "wand 102") coupled to an electrosurgical controller 104 (hereinafter "controller 104"). The wand 102 comprises an elongate shaft 106 that defines distal end 108. The elongate shaft 106 further defines a handle or proximal end 110, where a physician grips the wand 102 during surgical procedures. The wand 102 further comprises a flexible multi-conductor cable 112 housing one or more electrical leads (not specifically shown in FIG. 1), and the flexible multi-conductor cable 112 terminates in a wand connector 114. As shown in FIG. 1, the wand 102 couples to the controller 104, such as by a controller connector 120 on an outer surface of the enclosure 122 (in the illustrative case of FIG. 1, the front surface).

Though not visible in the view of FIG. 1, in some embodiments the wand 102 has one or more internal fluid conduits coupled to the externally accessible tubular members. As illustrated, the wand 102 has a flexible tubular member 116, used to provide aspiration at the distal end 108 of the wand (via a suction lumen—not shown here). In accordance with example systems, the tubular member 116 couples to a peristaltic pump 118, which peristaltic pump 118 is illustratively shown as an integral component with the controller 104 (i.e., residing at least partially within the enclosure 122 of the controller 104). In other embodiments, an enclosure for the peristaltic pump 118 may be separate from the enclosure 122 for the controller 104 (as shown by dashed lines in the figure)(e.g., bolted to the outside of the enclosure), but in any event the peristaltic pump may be operatively coupled to the controller 104.

The example peristaltic pump 118 comprises a rotor portion 124 (hereafter just "rotor 124") as well as a stator portion 126 (hereafter just "stator 126"). The flexible tubular member 116 couples within the peristaltic pump 118 between the rotor 124 and the stator 126, and movement of the rotor 124 against the flexible tubular member 116 causes fluid movement toward the discharge 128. While the illustrative peristaltic pump 118 is shown with a two-roller rotor 124, varying types of peristaltic pumps 118 may be used (e.g., a five-roller peristaltic pump). In other example systems, the tubing 116 may couple to any source of vacuum, such as a vacuum source available in most hospital and/or surgical centers.

Still referring to FIG. 1, a display device or interface device 130 is visible through the enclosure 122 of the controller 104. The example interface device 130 may be used select operational modes of the controller 104 (either directly on the interface device 130 or by way of related buttons 132), and the interface device 130 may also be the location where information is provided to the surgeon. For example, the interface device 130 may display an indication that the active electrode of the wand 102 is approaching, has reached, or has exceeded the useful life of the active electrode. Various aspects of determining the state of the useful life of the electrode are discussed in more detail below.

In some embodiments the electrosurgical system 100 also comprises a foot pedal assembly 134. The foot pedal assembly 134 may comprise one or more pedal devices 136 and 138, a flexible multi-conductor cable 140 and a pedal connector 142. While only two pedal devices 136 and 138 are shown, one or more pedal devices may be implemented. The enclosure 122 of the controller 104 may comprise a corresponding connector 144 that couples to the pedal connector 142. A physician may use the foot pedal assembly 134 to control various aspects of the controller 104, such as the mode of ablation. For example, pedal device 136 may be used for on-off control of the application of radio frequency (RF) energy to the wand 102, and more specifically for control of energy in a mode of ablation. Further, pedal device 138 may be used to control and/or set the mode of ablation of the electrosurgical system. For example, actuation of pedal device 138 may switch between energy levels created by the controller 104 and aspiration volume created by the peristaltic pump 118. In certain embodiments, control of the various operational or performance aspects of controller 104 may be activated by selectively depressing finger buttons located on handle 110 of wand 102 (the finger buttons not specifically shown so as not to unduly complicate the figure).

The electrosurgical system 100 of the various embodiments may have a variety of modes of ablation which employ Coblation® technology. In particular, the assignee of the present disclosure is the owner of Coblation® technology. Coblation® technology involves the application of a radio frequency (RF) signal between one or more active electrodes and one or more return electrodes of the wand 102 to develop high electric field intensities in the vicinity of the target tissue. The electric field intensities may be sufficient to vaporize an electrically conductive fluid over at least a portion of the one or more active electrodes in the region between the one or more active electrodes and the target tissue. The electrically conductive fluid may be inherently present in the body, such as blood, or in some cases extracellular or intracellular fluid. In other embodiments, the electrically conductive fluid may be a liquid or gas, such as isotonic saline. In some embodiments, such as surgical procedures involving a knee or shoulder, the electrically conductive fluid is delivered in the vicinity of the active electrode and/or to the target site by a delivery system separate and apart from the system 100.

When the electrically conductive fluid is heated to the point that the atoms of the fluid vaporize faster than the atoms recondense, a gas is formed. When sufficient energy is applied to the gas, the atoms collide with each other causing a release of electrons in the process, and an ionized gas or plasma is formed (the so-called "fourth state of matter"). Stated otherwise, plasma may be formed by heating a gas and ionizing the gas by driving an electric current through the gas, or by directing electromagnetic waves into the gas. The methods of plasma formation give energy to free electrons in the plasma directly, electron-atom collisions liberate more electrons, and the process cascades until the desired degree of ionization is achieved. A more complete description of plasma can be found in Plasma Physics, by R. J. Goldston and P. H. Rutherford of the Plasma Physics Laboratory of Princeton University (1995), the complete disclosure of which is incorporated herein by reference.

As the density of the plasma becomes sufficiently low (i.e., less than approximately 1020 atoms/cm$^3$ for aqueous solutions), the electron mean free path increases such that subsequently injected electrons cause impact ionization within the plasma. When the ionic particles in the plasma layer have sufficient energy (e.g., 3.5 electron-Volt (eV) to 5 eV), collisions of the ionic particles with molecules that make up the target tissue break molecular bonds of the target tissue, dissociating molecules into free radicals which then combine into gaseous or liquid species. By means of the molecular dissociation (as opposed to thermal evaporation or carbonization), the target tissue is volumetrically removed through molecular dissociation of larger organic molecules into smaller molecules and/or atoms, such as hydrogen, oxygen, oxides of carbon, hydrocarbons and nitrogen compounds. The molecular dissociation completely removes the tissue structure, as opposed to dehydrating the tissue material by the removal of liquid within the cells of the tissue and extracellular fluids, as occurs in related art electrosurgical desiccation and vaporization. A more detailed description of the molecular dissociation can be found in commonly assigned U.S. Pat. No. 5,697,882 the complete disclosure of which is incorporated herein by reference.

The energy density produced by electrosurgical system 100 at the distal end 108 of the wand 102 may be varied by adjusting a variety of factors, such as: the number of active electrodes; electrode size and spacing; electrode surface area; asperities and/or sharp edges on the electrode surfaces; electrode materials; applied voltage; current limiting of one or more electrodes (e.g., by placing an inductor in series with an electrode); electrical conductivity of the fluid in contact with the electrodes; density of the conductive fluid; the temperature of the conductive fluid; and other factors. Accordingly, these factors can be manipulated to control the energy level of the excited electrons. Since different tissue structures have different molecular bonds, the electrosurgical system 100 may be configured to produce energy sufficient to break the molecular bonds of certain tissue but insufficient to break the molecular bonds of other tissue. For example, fatty tissue (i.e. adipose) has double bonds that require an energy level higher than 4 eV to 5 eV (i.e., on the order of about 8 eV) to break. Accordingly, the Coblation® technology in some modes of ablation does not ablate such fatty tissue; however, the Coblation® technology at the lower energy levels may be used to effectively ablate cells to release the inner fat content in a liquid form. Other modes of ablation may have increased energy such that the double bonds can also be broken in a similar fashion as the single bonds (e.g., increasing voltage or changing the electrode configuration to increase the current density at the electrodes). A more complete description of the various phenomena can be found in commonly assigned U.S. Pat. Nos. 6,355,032, 6,149,120 and 6,296,136, the complete disclosures of which are incorporated herein by reference.

Figure 2:
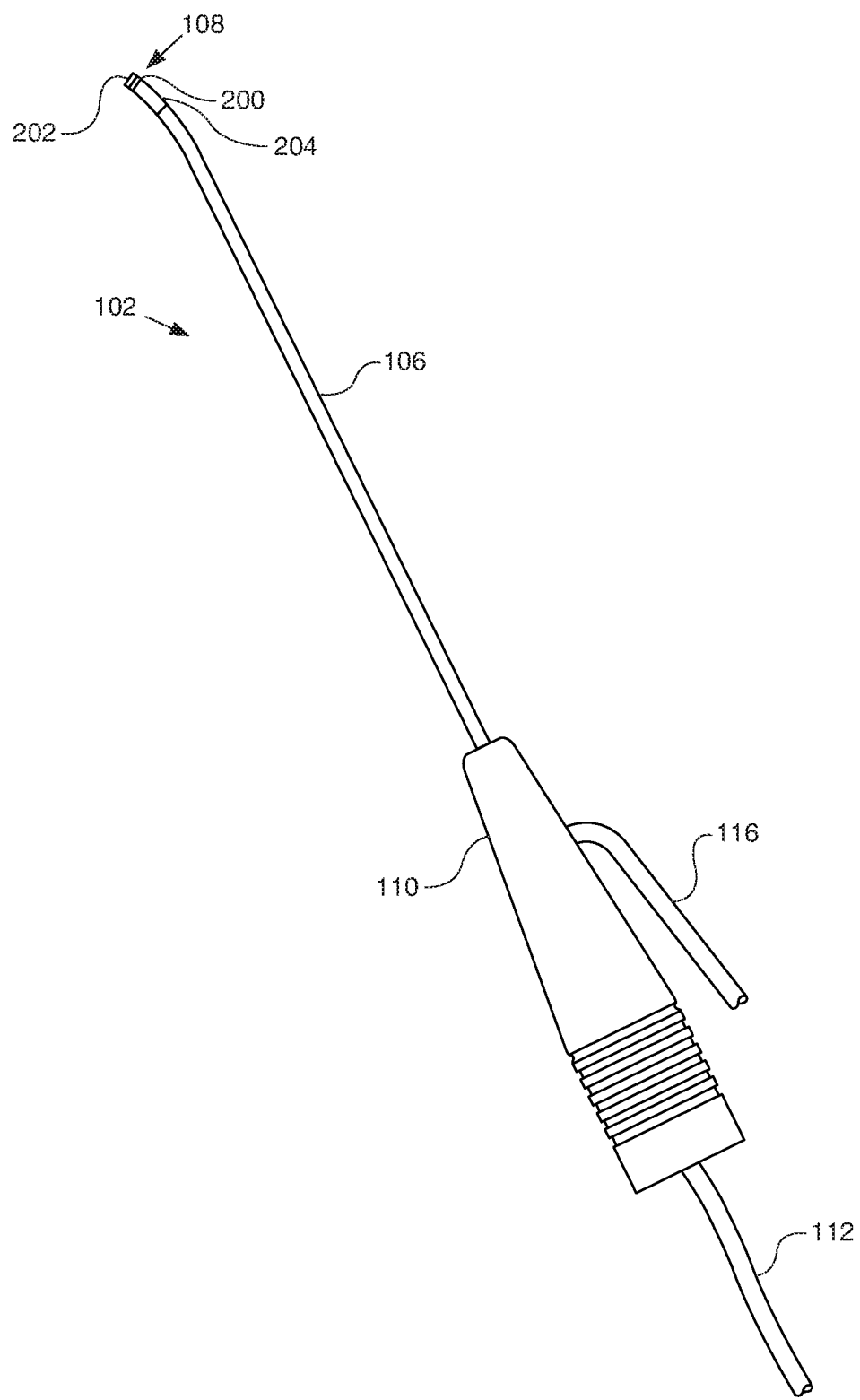
FIG. 2 shows an elevation view of an electrosurgical wand in accordance with at least some embodiments.

FIG. 2 shows an elevation view of wand 102 in accordance with example systems. In particular, wand 102 comprises elongate shaft 106 which may be flexible or rigid, a handle 110 coupled to the proximal end of the elongate shaft 106, and an electrode support member 200 coupled to the distal end of elongate shaft 106. Also visible in FIG. 2 is the flexible tubular member 116 extending from the wand 102 and the multi-conductor cable 112. The wand 102 comprises an active electrode 202 disposed on the distal end 108 of the elongate shaft 106. Active electrode 202 may be coupled to an active or passive control network within controller 104 (FIG. 1) by means of one or more insulated electrical connectors (not shown) in the multi-conductor cable 112. The active electrode 202 is electrically isolated from a common or return electrode 204 which is disposed on the shaft proximal of the active electrode 202, in some example systems within 1 millimeter (mm) to 25 mm of the distal tip. Proximally from the distal tip, the return electrode 204 located along the elongate shaft 106 of the wand 102. The support member 200 is positioned distal to the return electrode 204 and may be composed of an electrically insulating material such as epoxy, plastic, ceramic, silicone, glass or the like. Support member 200 extends from the distal end 108 of elongate shaft 106 (usually about 1 to 20 mm) and provides support for active electrode 202.

Figure 3:
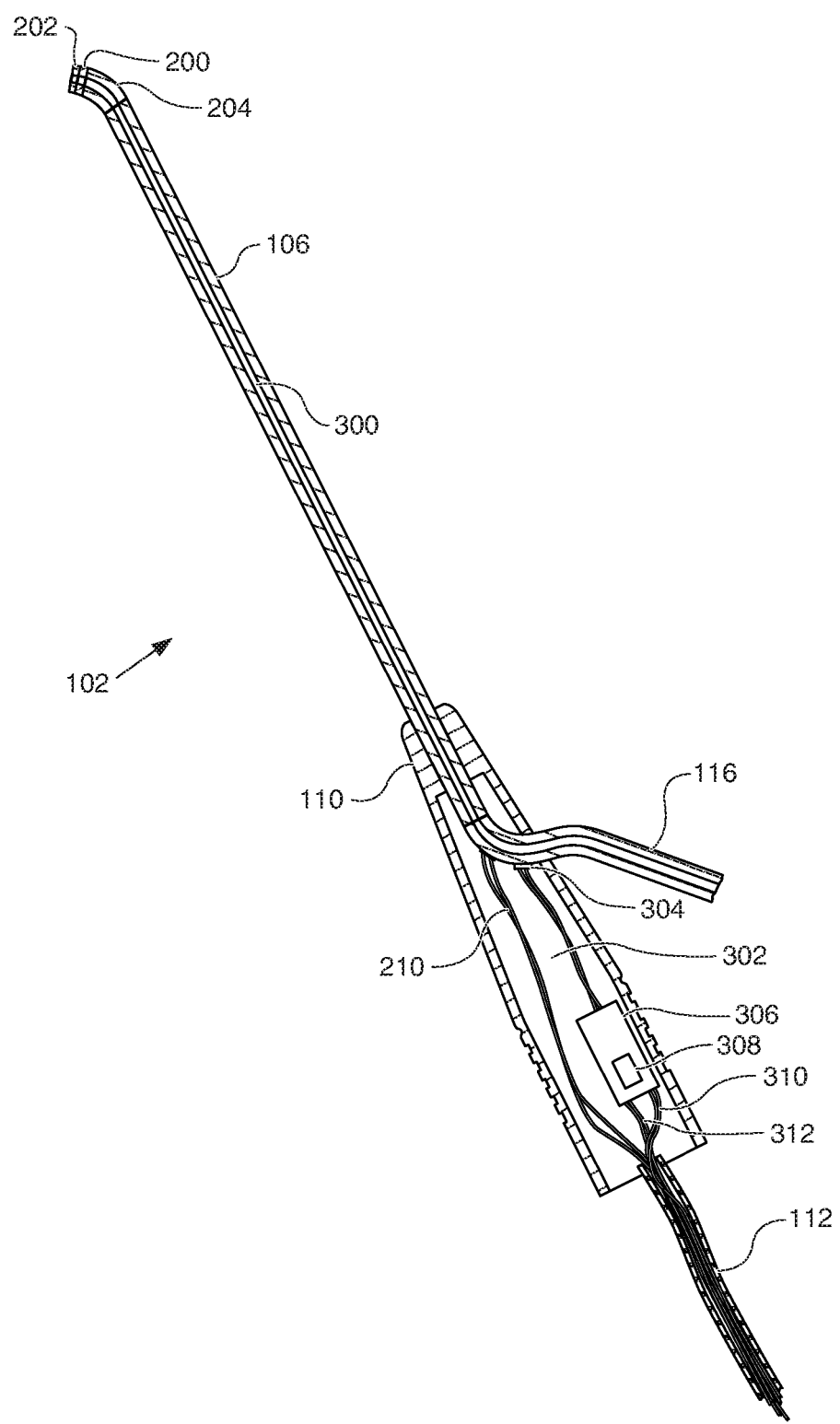
FIG. 3 shows a cross-sectional elevation view of an electrosurgical wand in accordance with at least some embodiments.

FIG. 3 shows a cross-sectional elevation view of the wand 102 in accordance with example embodiments. In particular, wand 102 comprises a suction lumen 300 defined within the elongate shaft 106. In the example wand 102 of FIG. 3, the inside diameter of the elongate shaft 106 defines the suction lumen 300, but in other cases a separate tubing within the elongate shaft 106 may define the suction lumen 300. The suction lumen 300 may be used for aspirating excess fluids, gas, bubbles, tissue fragments, and/or products of ablation from the target site through one or more apertures in or around the active electrode 202. Suction lumen 300 extends into the handle 110 and fluidly couples to the flexible tubular member 116 for coupling to the peristaltic pump 118 (FIG. 1) or other source of aspiration. Handle 110 also defines an inner cavity 302 within which electrical conductors 210 may reside, where the electrical conductors 210 may extend into the multi-conductor cable 112 and ultimately couple to the controller 104 (FIG. 1). The electrical conductors 210 likewise extend through the elongate shaft and couple, one each, to the return electrode 204 and the active electrode 202, but the electrical conductors 210 are not shown to reside within the elongate shaft 106 so as not to unduly complicate the figure.

In some systems, the wand 102 may further comprise a temperature measurement device 304 positioned to measure a temperature associated with the fluid drawn in from the vicinity of the active electrode. In the example system of FIG. 3, temperature sensor 304 is in operational relationship to the flexible tubular member 116. As illustrated in FIG. 3, the temperature measurement device 304 resides within the inner cavity 302 defined by the handle 110, but the temperature measurement device 304 may be placed at any suitable location. As illustrated, the temperature measurement device 304 abuts an outer surface of the tubular member 116 such that as fluids travel within the tubular member 116 past the location of the temperature measurement device 304, localized temperature changes can be read. Since a concern for injury is from the tubing outer wall to a patient or clinician's skin as the tubing extends away from the probe handle, a temperature sensor 304 is preferably placed as shown. As illustrated, the temperature measurement device 304 abuts an outer surface of the tubular member 116 such that as fluids travel within the tubular member 116 past the location of the temperature measurement device 304, localized temperature changes can be read. The temperature measurement device 304 may take any suitable form, such as a resistive thermal device (RTD), a thermistor, an optical temperature probe, or a thermocouple. Temperature measured by the temperature measurement device 304 may be useful in a variety of operational circumstances, such as part of the determination of clog detection or fluid flow disruption, both of which are discussed more below.

Still referring to FIG. 3, in example systems the wand 102 may have a processor 306 disposed within inner cavity 302. The processor 306 may be a microcontroller from any of a variety of available sources, such as one of the many microcontrollers available from Freescale Semiconductors, Inc. of Austin, Tex. The processor 306 may have onboard non-volatile memory 308 within which various programs and data may be stored. In example systems, the non-volatile memory 308 may store a program that, when executed by the processor, causes the processor 306 to periodically receive an output from the temperature measurement device 304 (electrically coupled to the processor 306) and then digitally send the temperature values (or values indicative of temperature) to the controller 104 by way of conductors 310. The processor 306 may be powered from the controller 104 through the multi-conductor cable 112, such as by conductors 312. The non-volatile memory 308 may also store parameters associated with temperature threshold values indicative of temperature, which parameters are discussed in greater detail below. In alternative embodiments, the wand may not include a processor and the temperature signal may be communicatively coupled directly to a processor within controller (described later).

Figure 4:
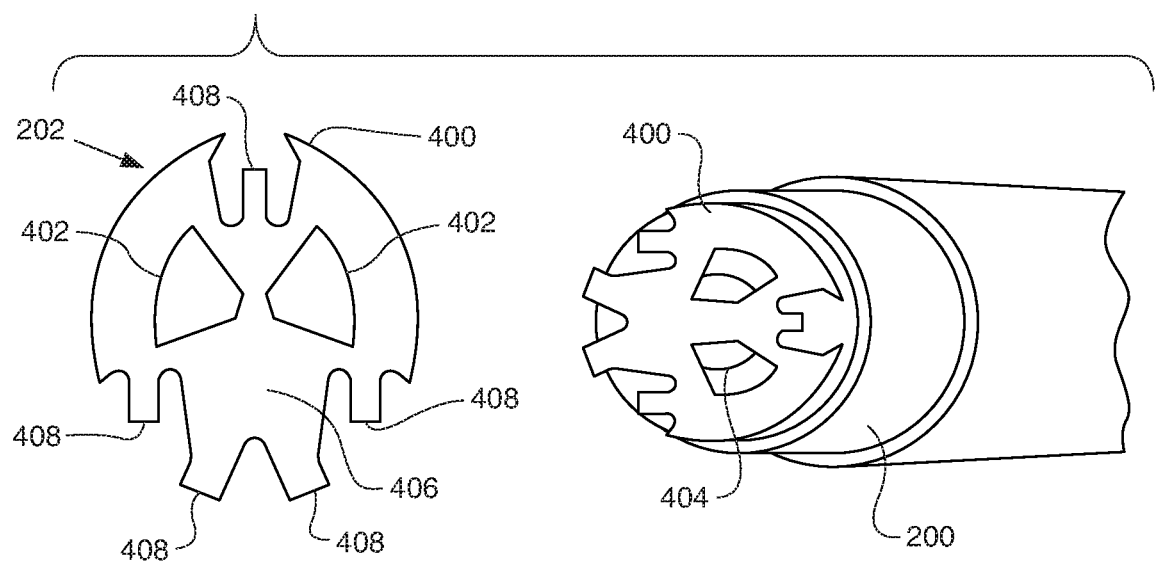
FIG. 4 shows both an elevation view of an active electrode and a perspective view of the distal end of a wand (including the active electrode) in accordance with at least some embodiments.

FIG. 4 shows an elevation view of an example active electrode (on the left), as well as a perspective view of the distal end of wand 102 (on the right), in accordance with example systems. In particular, active electrode 202 may be an active screen electrode 400 as shown in FIG. 4. Screen electrode 400 may comprise a conductive material, such as tungsten, titanium, molybdenum, platinum, or the like. Prior to the first use, screen electrode 400 may have a diameter in the range of about 0.5 to 8 mm, in some cases about 1 to 4 mm, and a thickness of about 0.05 to about 2.5 mm, in some cases about 0.1 to 1 mm. Screen electrode 400 may comprise a plurality of apertures 402 configured to rest over an aperture or distal opening 404 of the suction lumen. Apertures 402 enable the passage of aspirated excess fluids, bubbles, and gases from the ablation site, and the apertures 402 are large enough to enable ablated tissue fragments to pass through into suction lumen 300 (FIG. 3). As shown, screen electrode 400 has an irregular shape which increases the edge to surface-area ratio of the screen electrode 400. A large edge to surface-area ratio increases the ability of screen electrode 400 to initiate and maintain a plasma layer in conductive fluid because the edges generate higher current densities, which a large surface area electrode tends to dissipate power into the conductive media.

In the representative embodiment shown in FIG. 4, screen electrode 400 comprises a body 406 that rests over insulative support member 200 and the distal opening 404 to suction lumen 300. Screen electrode 400 further comprises tabs 408, in the example screen electrode 400 of FIG. 4, five tabs 408 are shown. The tabs 408 may rest on, be secured to, and/or be embedded in insulative support member 200. In certain embodiments, electrical connectors extend through insulative support member 200 and are coupled (i.e., via adhesive, braze, weld, or the like) to one or more of tabs 408 in order to secure screen electrode 400 to the insulative support member 200 and to electrically couple screen electrode 400 to controller 104 (FIG. 1). In example systems, screen electrode 400 forms a substantially planar tissue treatment surface for smooth resection, ablation, and sculpting of the meniscus, cartilage, and other tissues. In reshaping cartilage and meniscus, the physician often desires to smooth the irregular and ragged surface of the tissue, leaving behind a substantially smooth surface. For these applications, a substantially planar screen electrode treatment surface provides the desired effect.

Figure 5:
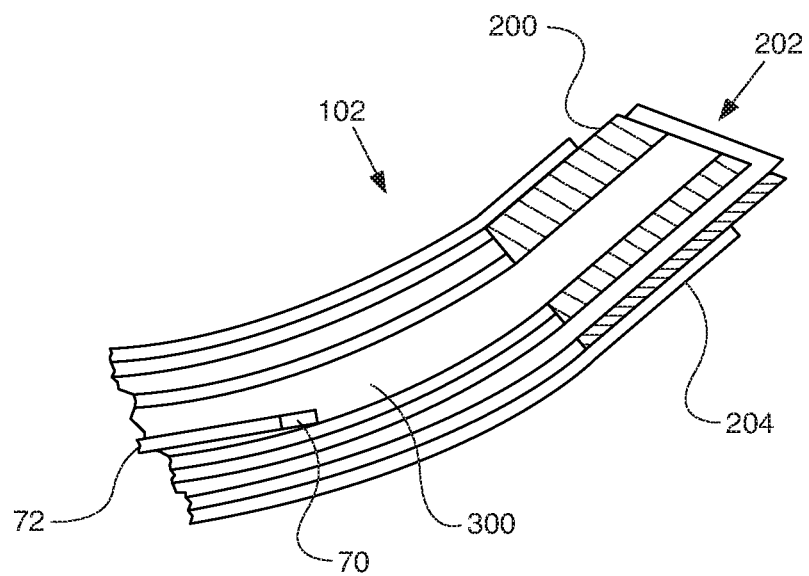
FIG. 5 shows a cross section view of a distal end of an electrosurgical probe with a temperature sensor in accordance with at least some embodiments.

FIG. 5 describes a distal end of an alternate representative probe 102 having a suction lumen 300 for aspirating electrically conductive fluid from the body or joint space with a temperature sensor 70 and conducting wire 72 positioned within the suction lumen 300 itself at a location disposed proximal the active electrode 202. Temperature sensor 70 may be disposed within the suction lumen 300 as shown, however this will measure the temperature of the fluid and not necessarily the temperature of the outer wall of the aspiration tube, as it extends from the handle, and so will have different temperature limits to the embodiment described in FIG. 3. In this example, a temperature of the electrically conductive fluid drawn from the vicinity of the active screen electrode 202 and then aspirated into suction lumen 300 may be measured as one method for determining a temperature of the fluid and suction tubing. Such temperature measurements may then be used to control the RF output and potentially also fluid flow through the device in order to prevent unintended damage to the device, patient or person that comes in contact with the suction tubing. In alternative embodiments temperature measurement device 70 may be disposed anywhere along the length of the inside lumen of the suction lumen or tubing, or may alternatively be embedded within the wall of the fluid transport element, including suction lumen or tubing.

The assignee of the current specification has a technology directed to a temperature measurement device on the elongate shaft 106 proximal of the return electrode 204. Reference is made to commonly assigned U.S. Pat. No. 8,696,659, entitled "ELECTROSURGICAL SYSTEM AND METHOD HAVING ENHANCED TEMPERATURE MEASUREMENT", the complete disclosure of which is incorporated herein by reference as if reproduced in full below. Such a temperature measurement device may be primarily responsive to the temperature surrounding the distal end 108, but spaced away from the active and return electrode, such a location for the temperature measurement device would also make the device secondarily responsive to temperature of fluid drawn into the suction lumen 300 from the vicinity of the active electrode. Thus, temperature measurements closer to the active electrode may also be used alone or in combination with the temperature measurement device 304 for the temperature aspects of the various embodiments.

Figure 6:
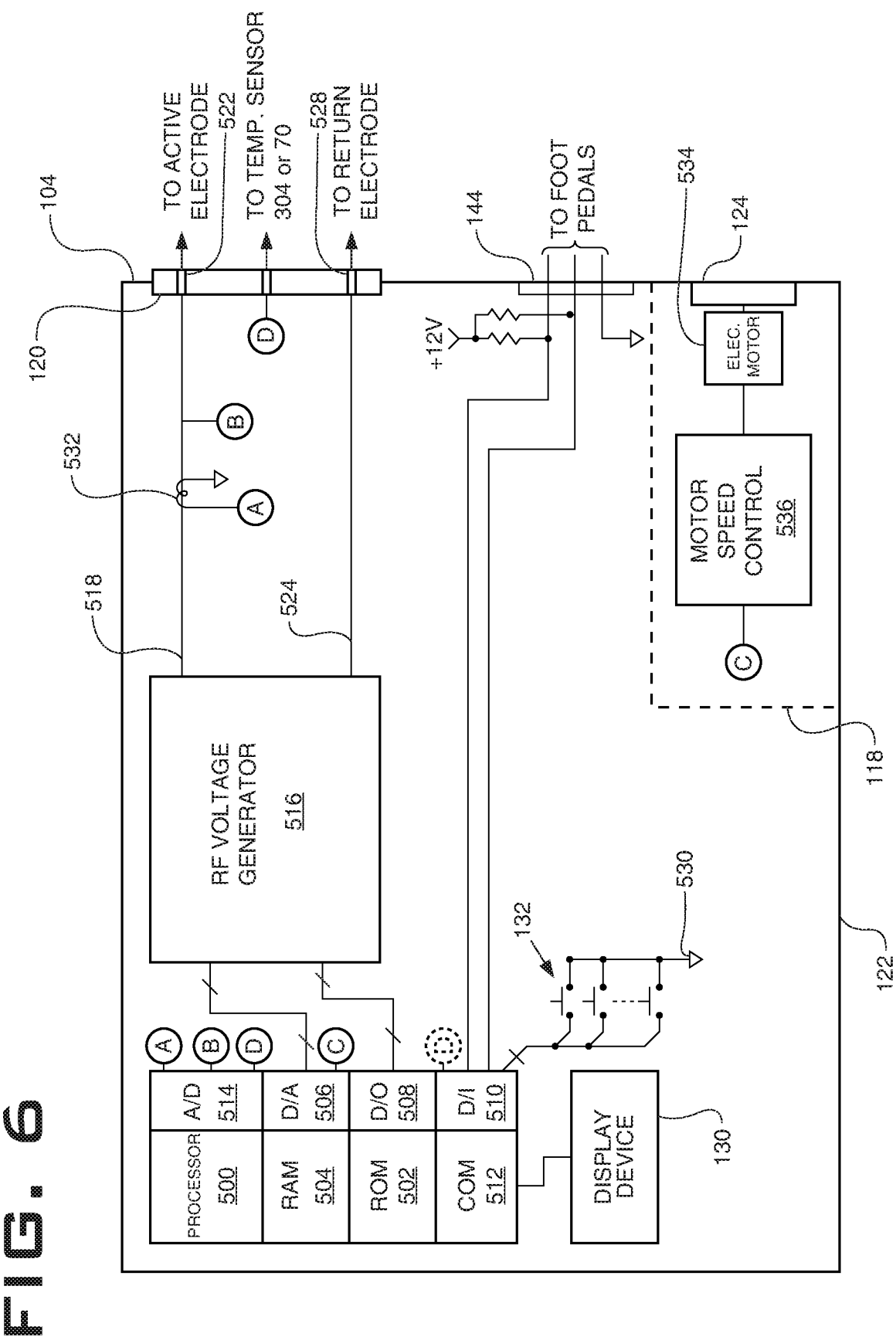
FIG. 6 shows a block diagram of an electrosurgical controller in accordance with at least some embodiments.

FIG. 6 shows an electrical block diagram of controller 104 in accordance with example systems. Reference is also made to commonly assigned U.S. patent application Ser. No. 14/339,621, entitled "ELECTROSURGICAL SYSTEM AND METHOD RELATED TO ELECTROSURGICAL PROCEDURES"; the complete disclosure of which is incorporated herein by reference as if reproduced in full below. In particular, the controller 104 comprises a processor 500. The processor 500 may be a microcontroller, and therefore the microcontroller may be integral with read-only memory (ROM) 502, random access memory (RAM) 504, digital-to-analog converter (D/A) 506, analog-to-digital converter (A/D) 514, digital outputs (D/O) 508, and digital inputs (D/I) 510. ROM 502 stores instructions executable by the processor 500. In particular, the ROM 502 may comprise a software program that, when executed, causes the controller to determine the presence or absence of various wand conditions, such as an over-temperature condition, elevated temperatures of suction tubing and/or partial disruption of fluid through a fluid transport apparatus of the wand. The RAM 504 may be the working memory for the processor 500, where data may be temporarily stored and from which instructions may be executed. Voltage generator 516 generates an alternating current (AC) voltage signal that is coupled to active electrode 202 of the wand 102 (FIG. 3). In some embodiments, the voltage generator defines an active terminal 518 which couples to electrical pin 520 in the controller connector 120, electrical pin in the wand connector (not shown), and ultimately to the active electrode 202 (FIG. 3). Likewise, the voltage generator defines a return terminal 524 which couples to electrical pin 526 in the controller connector 120, electrical pin in the wand connector (not shown), and ultimately to the return electrode 204 (also FIG. 3). The active terminal 518 is the terminal upon which the voltages and electrical currents are induced by the voltage generator 516, and the return terminal 524 provides a return path for electrical currents.

The voltage generator 516 delivers average energy levels ranging from several milliwatts to hundreds of watts per electrode, depending on the mode of ablation and state of the plasma proximate to the active electrode. In example systems, the voltage generator 516 in combination with the processor 500 are configured to initially set the energy output of the voltage generator 516 (e.g., by controlling output voltage) based on the mode of ablation selected by the surgeon, and in some cases the setpoint within the particular mode of ablation. Moreover, while in a selected mode of ablation and setpoint within the mode of ablation, the processor 500 and/or voltage generator 516 may make control changes to compensate for changes caused by use of the wand. A description of various voltage generators 516 can be found in commonly assigned U.S. Pat. Nos. 6,142,992 and 6,235,020, the complete disclosure of both patents are incorporated herein by reference for all purposes. Before proceeding, it is noted that the various embodiments of limiting the suction tubing temperature or detecting a partial clog, may be implemented on systems having a single mode of ablation. Stated otherwise, determining the presence of an over temperature condition or partial clog is not limited to systems having multiple modes of ablation.

During use of the controller 104, the electrode circuit (including the plasma created and maintained in operational relationship to the active electrode of a wand, the fluid between the active and return electrode, and the electrode-fluid interface) has or presents a certain amount of impedance to the flow of energy from the active electrode toward a return electrode. The impedance presented by the electrode circuit may be dependent on many factors, including but not limited to the thickness and volume of the plasma itself, the surface area of the active electrode, the surface area of the active electrode not covered by a vapor layer and directly in contact with the conductive fluid, and the volume flow of fluid and/or gasses away from the location of the plasma. In example systems, voltage generator 516 is a "constant voltage source", meaning that the voltage generator 516 provides the voltage requested by the processor 500 (at the frequency and duty cycle) largely independent of the impedance presented by the electrode circuit. In such systems, the controller 104 may comprise a mechanism to sense the electrical current provided to the active electrode. In the illustrative case of FIG. 6, sensing electrical current provided to the active electrode may be by way of a current sense transformer 532. In particular, current sense transformer 532 may have a conductor of the active terminal 518 threaded through the transformer such that the active terminal 518 becomes a single turn primary. Current flow in the single turn primary induces corresponding voltages and/or currents in the secondary. Thus, the illustrative current sense transformer 532 is coupled to the analog-to-digital converter 514 (as shown by the bubble A). Still referring to FIG. 6 (and also FIG. 1), controller 104 in accordance with example systems further comprises peristaltic pump 118. The peristaltic pump comprises rotor 124 mechanically coupled to a shaft of the electric motor 534. In some cases, and as illustrated, the rotor of the electric motor may couple directly to the rotor 124, but in other cases various gears, pulleys, and/or belts may reside between the electric motor 534 and the rotor 124. The electric motor 534 may take any suitable form, such as an AC motor, a DC motor, and/or a stepper-motor. To control speed of the shaft of the electric motor 534, and thus to control speed of the rotor 124 (and the volume flow rate at the wand), the electric motor 534 may be coupled to a motor speed control circuit 536. In the illustrative case of an AC motor, the motor speed control circuit 536 may control the voltage and frequency applied to the electric motor 534. In the case of a DC motor, the motor speed control circuit 536 may control the DC voltage applied to the electric motor 534. In the case of a stepper-motor, the motor speed control circuit 536 may control the current flowing to the poles of the motor, but the stepper-motor may have a sufficient number of poles, or is controlled in such a way, that the rotor 124 moves smoothly. Stated otherwise, the rotor 124 moves smoothly due to the high number of steps per turn.

The processor 500 couples to the motor speed control circuit 536, such as by way of the digital-to-analog converter 506 (as shown by bubble C). The processor 500 may be coupled in other ways as well, such as packet-based communication over the communication port 512. Thus, the processor 500, running a program, may read electrical current supplied on the active terminal 518, may read voltage supplied on the active terminal 518, and responsive thereto may make speed control changes (and thus volume flow rate changes) by sending speed commands to the motor speed control circuit 536. The motor speed control circuit 536, in turn, implements the speed control changes. Speed control changes may comprise changes in speed of the rotor 124 when desired, stopping the rotor 124 when desired, and in some modes of ablation temporarily reversing the rotor 124.

In some systems, the various predetermined values and temperatures are stored in a volatile memory of the controller 104. Once the controller 104 identifies the wand (either automatically, or by the user inputting the information using buttons 132 and/or display device 130), the appropriate predetermined values, and temperatures are read and applied during use. In this illustrative case, the temperatures sensor 304 is coupled to the analog-to-digital converter 514 (as shown by the bubble D). In other systems, the various values, and temperatures are stored on the wand 102. For example, and referring briefly to FIG. 3, the non-volatile memory 308 associated with the processor 306 may store the various predetermined values, and temperatures (for a single mode of ablation, or for multiple modes of ablation). The controller 104 may read data from the processor 306 (such as over 310), and then apply the data during the electrosurgical procedure. In this illustrative case, the temperatures sensor 304 may be coupled to the D/I 510 (as shown by the dashed bubble D).

Figure 7A:
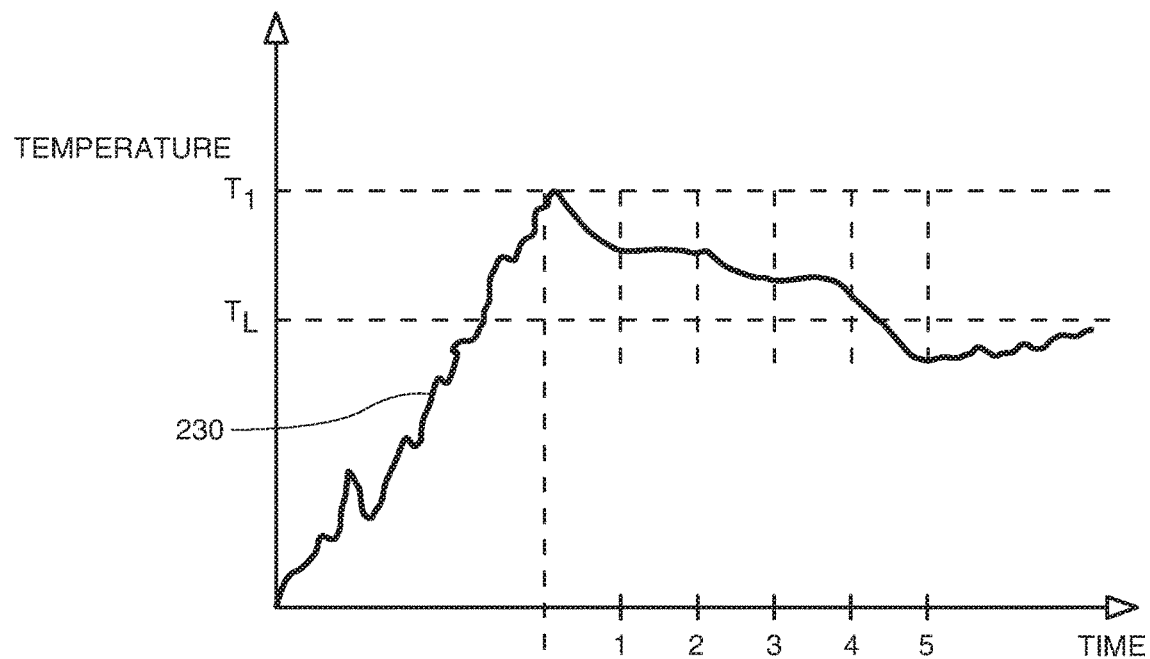
FIG. 7A is an illustrative graph showing a signal indicative of temperature versus time.

The non-volatile memory may be programmed to incorporate a set of multiple progressive temperature limits or thresholds that are below a temperature where potential injury could occur, should the tubing make contact with a patient, clinician or sensitive component. The controller 104 may comprise a processor that, upon receiving a signal indicative of a temperature threshold being exceeded, proceeds to a first over-temperature control, that includes modulating the RF output and may also include modulating fluid flow rate delivered from the pump 118. For example in FIGS. 7A and 7B, upon a temperature signal being received from the temperature measurement device 304 indicating the first threshold temperature T1 has been exceeded, the controller 104 may reduce or adjust the RF output delivered to active electrode 202, as shown in FIG. 7A, in a cyclic manner. In alternative embodiments, the system may deliver other forms of energy to an electrode or distal end of a device, such as DC heating or ultrasonic or microwave energy.

Controller 104 may be further configured to control a fluid flow rate associated with a fluid pump 118 (disclosed in FIG. 1). Illustrated in the chart of FIGS. 7A and 7B, while the sensed temperature 230 is less than the first threshold temperature T1, the controller 104 may control the fluid flow rate at a first pump flow rate or a first pump flow rate range that is set according the desired mode of the system and may include a dynamically controlled flow rate. Upon the sensed temperature value 230 reaching a first threshold temperature T1, the fluid flow rate may be automatically adjusted by controller 104 cycle between the first pump flow rate and a cooling flow rate. This cooling flow rate may be higher, lower or overlap with the first pump flow rate range. The cooling flow rate may a preprogrammed value depending on the mode the system is in and/or instrument being used. Present values of the cooling flow rate may be stored within a processor 306 in the wand for example. This cooling flow rate is configured to aid in cooling the wand 102 and fluid transport apparatus, however is also limited so as to reduce the likelihood of further aspirating debris and plasma by-products that may increase the clogged condition causing the elevated temperatures in the first place. This cooling rate may still be operable to continue to remove small debris disposed within the fluid transport apparatus. Exemplary cooling fluid rates may be between 60-90 mL/min.

Figure 7B:
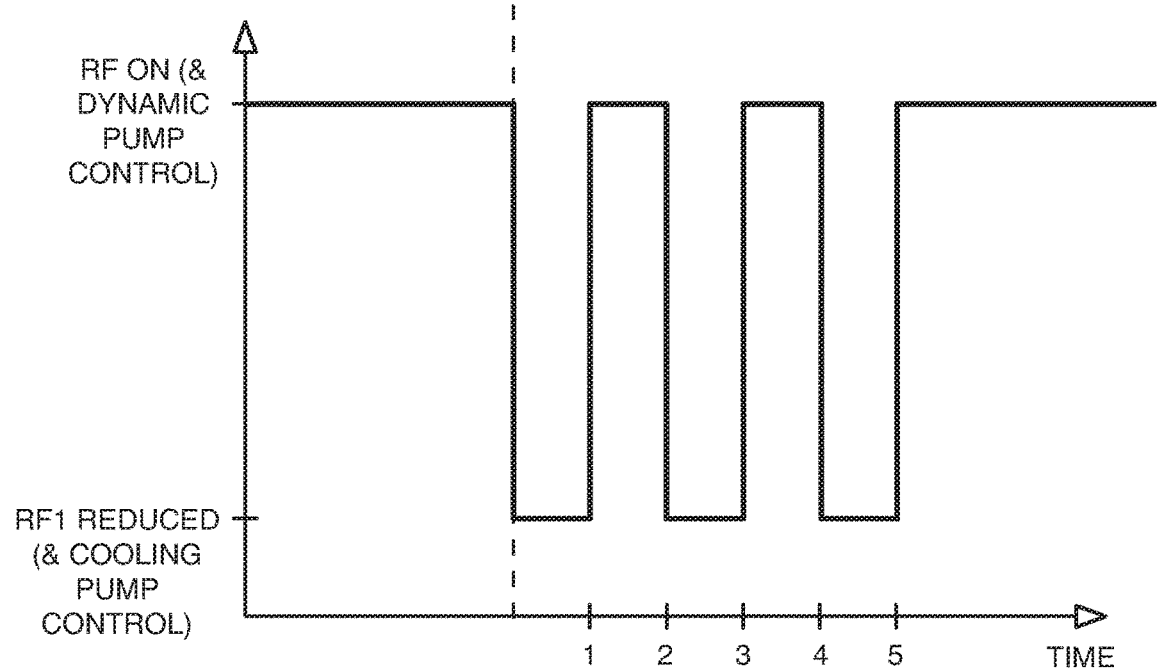
FIG. 7B is an illustrative graph showing changes in the RF and pump control system upon the temperature signal reaching a first threshold temperature T1.

As shown in FIGS. 7A and 7B, once a signal has been received indicative that a first threshold temperature T1 has been reached or exceeded, the controller 104 may adjust the RF energy delivery and pump speed in a cycling fashion. The energy delivery and pump speed may be cycled synchronously. The RF energy delivery may cycle between a first high frequency energy and a reduced high frequency energy; the first high frequency energy sufficient to treat tissue according to a selected mode and the reduced energy operable to limit the heating of the fluid (FIG. 7B). Overall however, this cycling is configured so that tissue will continue to be treated, and a plasma may still be present adjacent the active electrode at least some of the time. The fluid pump speed may be simultaneously cycled between a cooling flow rate and a first pump flow rate. Each cycle may have a duration that is adjustable between 0.5-4 seconds, each cycle including both a duration when the energy is reduced and/or flow rate is adjusted and a duration when energy is being delivered sufficient to treat tissue and/or the flow is at the first fluid flow rate; the controller 104 operable to adjust these cycle durations so that each pulse or cycle may have a total duration ranging between a cycle lasting between 0.5 and 4 seconds. As shown in FIG. 7B, each cycle may preferably last about 2 seconds. In alternatively envisioned embodiments the cycling may not have equal on and off times, and may have adjustable cycling times depending on the temperatures sensed or desired mode of the tissue effect. Visual or audible alarms may be triggered at this time to inform the user of this change. This cycling may continue until the temperature signal indicates that the sensed temperature 230 has dropped below a lower limit $T_L$, at which point the cycling may be suspended and RF delivery and fluid flow rates may return to the desired levels to treat tissue without interruption. The cycling rate is configured so as to aid in cooling the wand and aspiration tubing, while still providing a tissue effect in accordance with the desired mode. Exemplary values of $T_L$ may be approximately between 45° C. and 54° C., preferably 48° C., while approximate values of T1 may be between 48° C. and 56° C., preferably 50° C. These temperature values may vary depending on device being used, desired treatment mode and/or target tissue. In an alternative embodiment, the controller 104 may adjust or pulse the RF energy delivered but may not adjust the fluid flow rate, as reducing the RF energy delivery alone may be sufficient to reduce the sensed temperature. In alternative embodiments, the controller 104 may adjust the fluid flow rate and may not adjust the RF energy delivered.

As shown in FIGS. 8A and 8B, should the first over-temperature cycling operation as described above not be sufficient to reduce the sensed temperature 230, the non-volatile memory either within device 102 or controller 104 may store a second threshold temperature limit (T2) which may trigger a second over-temperature algorithm. As shown here, in certain conditions the measured temperature 230 may increase towards a second threshold temperature T2, despite initiating a first over-temperature cycling control. Upon the measured temperature 230 reaching or exceeding T2, the RF energy delivery may be automatically adjusted or suspended and/or the fluid flow rate may be adjusted by controller 104 to a cooling flow rate. The cooling flow rate may depend on the device, target tissue and preset mode of delivery and may be between 60-90 mL/min. No cycling may occur during this phase, and the energy may not return to treat tissue according to the desired mode until the sensed temperature 230 has dropped below the lower temperature threshold $T_L$. Visual or audible alarms may be triggered should this during the phase, so as to inform the user of the change in expected tissue treatment. Exemplary values of T2 may be approximately between 52° C. and 56° C., preferably 54° C.

The specification now turns to a description of an example implementation in greater detail. FIG. 9 shows a flow diagram of a method which may be implemented on the processor 500 of the controller 104. The method starts (900) and proceeds to supplying a first high frequency energy to an active electrode of an electrosurgical wand; drawing an electrically conductive fluid, from the vicinity of the active electrode and sensing a temperature signal indicative of a temperature of the electrically conductive fluid drawn from the vicinity of the active electrode (905) according to a selected mode of operation by the clinician, until either a clinician sends a message to the controller to cease or until the sensed temperature exceeds a first threshold temperature (T1) (910). If the sensed temperature reaches or exceeds T1, then the controller may direct the system to initiate a first over-temperature cycle including cycling the first high frequency energy supplied and possibly also cycling the fluid flow rate at which the electrically conductive fluid is drawn (920). If cycling the high frequency energy (and fluid flow rate) is operable to cool the sensed temperature to a lower threshold temperature (930), then the controller directs the system to suspend cycling and resume delivering energy according to the selected mode of operation (905). If cycling the high frequency energy allows the sensed temperature to continue to elevate to a second threshold level (940), the controller may direct the system to initiate a second over-temperature algorithm and suspend cycling, reduce the energy delivery (or turn it off) and potentially also set the fluid flow rate to a cooling flow rate (950), until the sensed temperature reaches the lower threshold temperature (960), whereupon energy delivery according the desired mode may be resumed (905).

FIG. 10 shows a flow diagram of a method which may be implemented on the processor 500 of the controller 104 to limit a temperature of a fluid drawn through a fluid transport element of an electrosurgical wand. The method starts (1000) and proceeds to drawing an electrically conductive fluid at a first fluid flow rate though a fluid transport element of an electrosurgical wand; delivering a high frequency energy to an active electrode of the electrosurgical wand, sufficient to treat a target tissue; and sensing a temperature associated with the electrically conductive fluid (1010); and upon sensing that the temperature associated with the electrically conductive fluid has reached a first threshold limit (1020), pulsing the step of drawing the electrically conductive fluid, between the first fluid flow rate and a cooling flow rate (1030); and upon sensing that the temperature associated with the electrically conductive fluid has reached either a second threshold limit or a lower threshold limit (1040), suspending the pulsing step (1050), the second threshold limit higher that the first threshold limit, and the lower threshold limit lower than the first threshold limit.

In some embodiments the controller may be programmed with a time limit or multiple time limits as to a duration of time the sensed temperature may be above a certain limit before shutting off the controller (and thereby the power supply) completely, or indicating a different alarm to the user.

Other modifications and variations can be made to the disclosed embodiments without departing from the subject invention. For example, other uses or applications are possible. Similarly, numerous other methods of controlling or characterizing instruments or otherwise treating tissue using electrosurgical probes will be apparent to the skilled artisan. Moreover, the instruments and methods described herein may be utilized in instruments for various regions of the body (e.g., shoulder, knee, etc.) and for other tissue treatment procedures (e.g., chondroplasty, menectomy, etc.). Thus, while the exemplary embodiments have been described in detail, by way of example and for clarity of understanding, a variety of changes, adaptations, and modifications will be obvious to those of skill in the art. Therefore, the scope of the present invention is limited solely by the appended claims.

While preferred embodiments of this disclosure have been shown and described, modifications thereof can be made by one skilled in the art without departing from the scope or teaching herein. The embodiments described herein are exemplary only and are not limiting. Because many varying and different embodiments may be made within the scope of the present inventive concept, including equivalent structures, materials, or methods hereafter thought of, and because many modifications may be made in the embodiments herein detailed in accordance with the descriptive requirements of the law, it is to be understood that the details herein are to be interpreted as illustrative and not in a limiting sense.

We claim:

1. An electrosurgical system comprising:
a controller comprising
a processor;
a memory coupled to the processor;
a voltage generator operatively coupled to the processor
a fluid flow pump operatively coupled to the processor and configured to control a fluid flow through a fluid aspiration element; and
an electrosurgical wand operatively coupled to an output of the voltage generator, the wand having a temperature sensor in operational relationship with the fluid aspiration element; the temperature sensor communicatively coupled to the processor;
wherein the memory stores a program that, when executed by the processor, causes the controller to:
deliver a first high frequency voltage to an active electrode of the electrosurgical wand;
control the fluid flow pump to draw an electrically conductive fluid through the fluid aspiration element at a first flow rate range, away from the vicinity of the active electrode;
sense a temperature signal indicative of a temperature of the electrically conductive fluid drawn from the vicinity of the active electrode with the temperature sensor; and
initiate a first over-temperature cycle, including controlling the fluid flow pump and voltage generator so as to deliver a pulsed voltage and a pulsed fluid flow rate, upon the processor receiving a signal indicative that the temperature exceeds a first threshold temperature; wherein the first threshold temperature is configured to detect a temperature indicative of an inadequate fluid flow condition through the fluid aspiration element and the first over-temperature cycle is configured to regulate said temperature.

2. The system of claim 1 wherein a pulsed fluid flow rate comprises modulating between the first flow rate range and a cooling flow rate.

3. The system of claim 2 wherein the cooling flow rate is configured to reduce the temperature of the fluid aspiration element while minimally aspirating debris relative to the first flow rate range.

4. The system of claim 1, wherein the first high frequency energy and the first flow rate range are configured to cooperate with each other to form a plasma adjacent the active electrode, the plasma configured to treat tissue.

5. The system of claim 2 wherein the
pulsed voltage comprises modulating the high frequency voltage between the first high frequency voltage and a second lower high frequency voltage, so as to continue to treat tissue and wherein the first over-temperature cycle comprises a constant frequency cycle switching between a first portion of the cycle wherein the energy is delivered at the first high frequency voltage simultaneously with the aspiration flow rate drawn at the first flow rate range and a second portion of the cycle wherein the energy is delivered at the second lower high frequency voltage simultaneously with the aspiration flow rate at the cooling flow rate.

6. The system of claim 1, wherein the memory stores a program that, when executed by the processor, causes the controller to pulse the voltage generator and fluid flow pump to
pulse at a rate between 0.25-2 pulses per second.

7. The system of claim 1, wherein the memory stores a program that, when executed by the processor, further causes the controller to:
suspend delivering high frequency energy upon the temperature exceeding a second threshold temperature, higher than the first threshold temperature.

8. The system of claim 7 wherein the memory stores a program that, when executed by the processor, further causes the controller to:
maintain a cooling flow rate until the temperature cools to a lower threshold temperature, upon the temperature of the electrically conductive fluid exceeding the second threshold temperature, the lower threshold temperature lower than the first threshold temperature.

9. The system of claim 7 wherein the memory stores a program that, when executed by the processor, further causes the controller to:
maintain the step of suspending delivering the high frequency energy until the temperature reaches a lower threshold temperature, the lower threshold temperature lower than the first threshold temperature.

10. The system of claim 1 wherein the temperature sensor is disposed on an outer surface of the fluid aspiration element and within a handle of the electrosurgical wand.

11. The system of claim 10 wherein the temperature sensor is directly coupled to an external surface of the fluid aspiration element.

12. An electrosurgical system comprising:
a controller comprising
a processor;
a memory communicably coupled to the processor;
a voltage generator operatively coupled to the processor
a fluid flow pump operatively coupled to the processor and configured to control a fluid flow through a fluid aspiration element; and
an electrosurgical wand operatively coupled to an output of the voltage generator;
a temperature sensor operatively coupled to the fluid aspiration element the temperature sensor for detecting an inadequate fluid flow condition through the fluid aspiration element and communicatively coupled to the processor;
wherein the memory stores a program that, when executed by the processor, causes the controller to:
deliver a first high frequency voltage to an active electrode of the electrosurgical wand;
control the pump to draw an electrically conductive fluid through the fluid aspiration element at a first flow rate range from the vicinity of the active electrode;
receive a signal from the temperature sensor; and
control the fluid pump and voltage generator so as to synchronously pulse both the voltage supplied and the fluid flow rate upon the processor receiving a signal indicative that a temperature exceeds a first threshold temperature and thereby an inadequate fluid flow condition.

13. The system of claim 12 wherein pulsing the fluid flow rate modulates the fluid flow rate between the first flow rate range and a cooling flow rate.

14. The system of claim 13 wherein the cooling flow rate is configured to aid in cooling the temperature while minimally aspirating debris through the fluid aspiration element.

15. The system of claim 12, wherein the first high frequency energy and the first flow rate range are configured to cooperate with each other to ablate tissue.

16. The system of claim 12 wherein the memory stores a program that, when executed by the processor, causes the controller to:
control the voltage generator to pulse the high frequency voltage between the first high frequency voltage and a second lower high frequency voltage, while continuing to ablate tissue.

17. The system of claim 12, wherein the memory stores a program that, when executed by the processor, causes the controller to:
control the voltage generator and fluid flow rate to synchronously pulse at a rate between 0.25-2 pulses per second.

18. The system of claim 12, wherein the memory stores a program that, when executed by the processor, further causes the controller to:
suspend the high frequency energy delivery upon the temperature reaching or exceeding a second threshold temperature, higher than the first threshold temperature; and
maintain the step of suspending until the temperature cools to a lower threshold temperature, the lower threshold temperature lower than the first threshold temperature.

19. The system of claim 18 wherein the memory stores a program that, when executed by the processor, further causes the controller to:
maintain a cooling flow rate upon the temperature reaching or exceeding the second threshold temperature, and maintain the cooling flow rate until the processor receives a signal indicative of a temperature at or below a lower threshold temperature, the lower threshold temperature lower than the first threshold temperature.

20. An electrosurgical system comprising:
a controller comprising
a processor,
a memory communicably coupled to the processor;
a voltage generator for delivering a high frequency voltage output, operatively coupled to the processor
a fluid flow pump operatively coupled to the processor and configured to control a fluid flow through a fluid suction tube; and
an electrosurgical wand operatively coupled to an output of the voltage generator;
a temperature sensor directly coupled to an external surface of the fluid suction tube and communicatively coupled to the processor, for detecting high temperature conditions of the external surface;
wherein the memory stores a program that, when executed by the processor, causes the controller to:
deliver a first high frequency voltage to an active electrode of the electrosurgical wand;
control the pump to draw an electrically conductive fluid through the fluid suction tube at a first flow rate range from the vicinity of the active electrode;
receive a signal from the temperature sensor; and
upon the processor receiving a signal indicative that a temperature meets or exceeds a first threshold temperature, control the fluid pump to modulate the fluid flow and the voltage generator to modulate the output voltage so as to regulate the temperature of the fluid suction tube external surface.

21. The system of claim 20 wherein the processor controls the fluid pump to modulate the fluid flow between a first and second flow rate at a first frequency and also modulate the output voltage between a first and second output voltage at the first frequency.

* * * * *